United States Patent
Kata

(10) Patent No.: US 10,188,597 B1
(45) Date of Patent: Jan. 29, 2019

(54) HAIR COLOR STAIN REMOVER AND METHOD OF USE

(71) Applicant: Kamakshi Kata, Allen, TX (US)

(72) Inventor: Kamakshi Kata, Allen, TX (US)

(*) Notice: Subject to any disclaimer, the term of this patent is extended or adjusted under 35 U.S.C. 154(b) by 0 days.

(21) Appl. No.: 15/908,694

(22) Filed: Feb. 28, 2018

Related U.S. Application Data

(60) Provisional application No. 62/464,761, filed on Feb. 28, 2017.

(51) Int. Cl.

| | |
|---|---|
| *C11D 1/02* | (2006.01) |
| *C11D 3/32* | (2006.01) |
| *C11D 3/382* | (2006.01) |
| *C11D 3/43* | (2006.01) |
| *A61K 8/9789* | (2017.01) |
| *A61Q 19/10* | (2006.01) |
| *A61K 8/368* | (2006.01) |
| *A61K 8/44* | (2006.01) |
| *A61K 8/36* | (2006.01) |
| *A61K 8/34* | (2006.01) |
| *C11D 3/20* | (2006.01) |
| *C11D 3/38* | (2006.01) |
| *C11D 3/48* | (2006.01) |

(52) U.S. Cl.
CPC ............ *A61K 8/9789* (2017.08); *A61K 8/345* (2013.01); *A61K 8/36* (2013.01); *A61K 8/368* (2013.01); *A61K 8/44* (2013.01); *A61Q 19/10* (2013.01); *C11D 1/02* (2013.01); *C11D 3/2065* (2013.01); *C11D 3/2079* (2013.01); *C11D 3/32* (2013.01); *C11D 3/38* (2013.01); *C11D 3/382* (2013.01); *C11D 3/48* (2013.01)

(58) Field of Classification Search
CPC ....... C11D 1/02; C11D 3/2065; C11D 3/2079; C11D 3/32; C11D 3/38; C11D 3/382; C11D 3/48
USPC ....... 510/126, 136, 137, 138, 158, 159, 501, 510/505
See application file for complete search history.

(56) References Cited

U.S. PATENT DOCUMENTS

| | | | | |
|---|---|---|---|---|
| 6,113,929 | A * | 9/2000 | Karl ......................... | C11D 3/14 424/400 |
| 6,200,937 | B1 * | 3/2001 | Brennan ................ | A61K 8/416 510/119 |
| 8,173,583 | B2 * | 5/2012 | Garcia Castro ........ | A61K 8/817 424/401 |
| 2016/0015031 | A1 * | 1/2016 | Pesaro ..................... | A61K 8/35 424/65 |
| 2016/0143825 | A1 * | 5/2016 | Pesaro ..................... | A61K 8/33 424/55 |

* cited by examiner

*Primary Examiner* — Gregory R Delcotto
(74) *Attorney, Agent, or Firm* — Eldredge Law Firm, LLC; Richard Eldredge; Beth Felix

(57) ABSTRACT

A hair color stain remover formula, having by volume about 67.9999% Witch Hazel Extract; about 20.0% Glycerin; about 8.8% Distilled Water; about 3.0% Sodium Cocoyl Glycinate; about 0.1% Potassium Sorbate; about 0.1% Sodium Benzoate; and about 0.0001% Green Tea Extract.

1 Claim, 1 Drawing Sheet

101

| | |
|---|---|
| Witch Hazel Extract | 67.9999 % |
| Glycerin | 20.0000 % |
| DI Water | 8.8000 % |
| Sodium Cocoyl Glycinate | 3.0000 % |
| Potassium Sorbate | 0.1000 % |
| Sodium Benzoate | 0.1000 % |
| Green Tea Extract | 0.0001 % |
| | 100.0000 % |

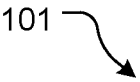
| | |
|---|---|
| Witch Hazel Extract | 67.9999 % |
| Glycerin | 20.0000 % |
| DI Water | 8.8000 % |
| Sodium Cocoyl Glycinate | 3.0000 % |
| Potassium Sorbate | 0.1000 % |
| Sodium Benzoate | 0.1000 % |
| Green Tea Extract | 0.0001 % |
| | 100.0000 % |

HAIR COLOR STAIN REMOVER AND METHOD OF USE

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 1 is a formula in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depict a formula for hair color stain remover on skin.

In the preferred embodiment of the formula 101 includes 67.9999 percent witch hazel extract, 20 percent glycerin, 8.8 percent distilled water, 3.0 percent sodium cocoyl glycinate, 0.10 percent potassium sorbate, 0.10 percent sodium benzoate, and 0.0001 percent green tea extract.

One of the unique features believed characteristic of the present application is the combination of the above ingredients in the same or similar percentages. It should be appreciated that this formula provides a novel hair color stain remover, while being safe and non-toxic for use on the skin.

It should be noted that other alternative embodiments of the formula are possible and that these embodiments would include the following ranges for the ingredients: witch hazel extract 20% to 80%, glycerin 1-20%, sodium cocoyl glycinate 0.5% to 10%, potassium sorbate 0.05% to 0.5%, sodium benzoate 0.05% to 0.5%, and any catechin containing extract 0.0001% to 1% with distilled water making up the remaining percentage of the formula. It will be appreciated that the preferred embodiment could be modified in the percentages in alternative embodiments in addition to other types of materials added therewith.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A hair color stain remover formula, comprising by volume:
   a) about 67.9999% Witch Hazel Extract;
   b) about 20.0% Glycerin;
   c) about 8.8% Distilled Water;
   d) about 3.0% Sodium Cocoyl Glycinate;
   e) about 0.1% Potassium Sorbate;
   f) about 0.1% Sodium Benzoate; and
   g) about 0.0001% Green Tea Extract.

* * * * *